United States Patent [19]

Novack et al.

[11] Patent Number: 5,525,733
[45] Date of Patent: Jun. 11, 1996

[54] PROCESS FOR PREPARING TETRAZOLE-5-CARBOXYLIC ACID DERIVATIVES

[75] Inventors: Vance Novack, Devon, Pa.; Neal Ward, Cranleigh; John C. Hanson, Redhill, both of United Kingdom

[73] Assignee: SmithKline Beecham PLC, Brentford, England

[21] Appl. No.: 495,562

[22] PCT Filed: Feb. 1, 1994

[86] PCT No.: PCT/EP94/00305

§ 371 Date: Aug. 1, 1995

§ 102(e) Date: Aug. 1, 1995

[87] PCT Pub. No.: WO94/18178

PCT Pub. Date: Aug. 18, 1994

[30] Foreign Application Priority Data

Feb. 5, 1993 [GB] United Kingdom ............ 9302331

[51] Int. Cl.$^6$ .................................................. C07D 257/04
[52] U.S. Cl. ............................................................ 548/253
[58] Field of Search ............................................. 548/253

[56] References Cited

U.S. PATENT DOCUMENTS 4,316,037 2/1982 Sellstedt et al. ........................ 548/253

FOREIGN PATENT DOCUMENTS 0323885 7/1989 European Pat. Off. .
2407207 5/1979 France .

*Primary Examiner*—David B. Springer
*Attorney, Agent, or Firm*—James M. Kanagy; Stuart R. Suter; Edward T. Lentz

[57] ABSTRACT

A process for preparing a compound of structure (I) or a hydrate or solvate thereof in which $R^1$ is $C_{1-6}$alkyl, optionally substituted phenyl or optionally substituted phenyl$C_{1-6}$alkyl, which comprises reacting an azide of the structure (II): $M^{\oplus}N_3^{\ominus}$ with a cyanoformate of the structure (III): $NC.CO_2R^1$ in which M is an alkali metal atom, and $R^1$ is as described for structure (I), to form an intermediate salt of structure (IV), in which $R^1$ is as described for structure (I) and M is as described for structure (II) followed by conversion of the salt (IV) to the free tetrazole (I) or to a hydrate or solvate thereof.

8 Claims, No Drawings

PROCESS FOR PREPARING TETRAZOLE-5-CARBOXYLIC ACID DERIVATIVES

This application is A 371 of PCT/EP94/00 305 filed Feb. 1, 1994.

The present invention relates to a novel process for preparing certain tetrazole compounds which are of use in the preparation of therapeutically active substances, in particular certain benzopyran compounds useful as inhibitors of 5-α-reductase and as leukotriene antagonists. The invention further relates to novel salt forms of the tetrazole compounds and to a process for preparing them.

Benzopyran compounds substituted by a tetrazole ring are described in the art, for example in EP 0173156-A. In addition, unpublished British Patent Application No. 9224922.6, filed 27 Nov. 1992, discloses a new process for preparing certain of the compounds of EP 0173156-A, in particular compounds of structure (A):

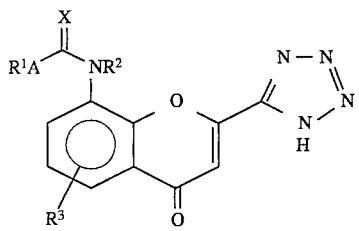

in which $R^1$ is, inter alia, $C_{1-20}$alkyl, $C_{2-20}$alkenyl, $C_{2-20}$alkynyl or a carboxylic group, X is oxygen or sulphur and $R^2$ and $R^3$ are, for example, hydrogen, by cyclisation of the corresponding intermediate compounds of structure (B):

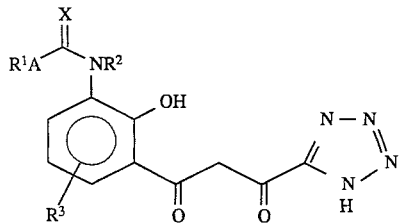

Compounds of structure (B) are described as being prepared by reaction of compounds of structure (C):

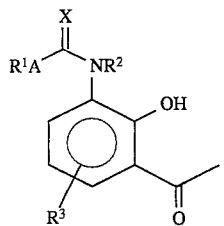

with a tetrazole derivative of structure (D):

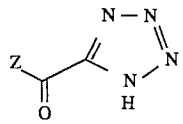

or salts thereof, in which Z is a leaving group. The compounds (D), for example where Z is an i-butoxy group, are described as being prepared from the corresponding tetrazole-5-carboxylic disodium salt by reaction with i-butyl chloroformate, followed by workup under acidic conditions. Preparation of salts of compounds (D) is not specifically described in GB 9224922.6 although, for example, the preparation of the sodium salt of ethyl-5-tetrazole carboxylate, in solution only, is described in the literature (Australian Journal of Chemistry (1984) 37, 2453-2468). In particular, the process described in GB 9224922.6 is used to prepare the compounds of structure (A1):

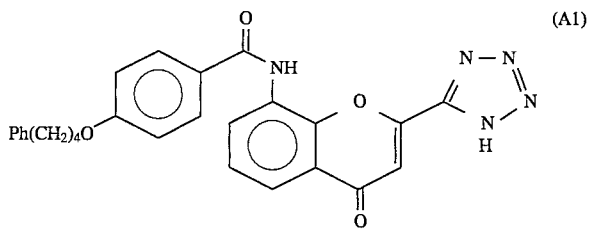

It has now been found that, by using novel methods described herein, the tetrazole compounds (D) and the salts thereof can be prepared in high yield and in high purity, avoiding the undesirable azide by-products associated with known methods.

The present invention therefore produces, in a first aspect, a process for preparing a compound of structure (I):

or a hydrate or solvate thereof in which $R^1$ is $C_{1-6}$alkyl, optionally substituted phenyl or optionally substituted phenyl$C_{1-6}$alkyl, which comprises combining an azide of structure (II) $M^{\oplus}N_3^{\ominus}$ in which M is an alkali metal atom, with a compound of structure (III) $NC.CO_2R^1$ in which $R^1$ is as described for structure (I), to form an intermediate compound of structure (IV):

in which $R^1$ is as described for structure (I) and M is as described for structure (II), followed by conversion of the salt (IV) to the free tetrazole (I) or to a hydrate or solvate thereof.

Suitably, $R^1$ is $C_{1-6}$alkyl, optionally substituted phenyl or optionally substituted phenyl$C_{1-6}$alkyl Preferably, $R^1$ is $C_{1-6}$alkyl, for example, methyl, ethyl, i-butyl or t-butyl.

Suitably, alkali metal atoms M include lithium, sodium and potassium. Preferably M is sodium or potassium.

Suitably, the reaction between the compounds of structures (II) and (III) is carried out in a suitable solvent in the presence of an acid, at a temperature of between ambient and reflux temperature of the solvent used, for as long as is required to take the reaction to completion. Suitable solvents include 2,6-lutidine and suitable acids include trifluoroacetic acid.

This process for preparing the tetrazole derivatives of structure (I) proceeding via the intermediate salts (IV) provides a more efficient and safer method of preparing compounds (I) than has been known before. Preparation of the tetrazole derivatives as described in EP 0323885 is a low yielding method and that described in Chem. Ber. (1975) 108, 887 is a very cumbersome method involving potential hazardous steps such as evaporation to dryness which makes them unsuitable for large scale use. In the present process, the salts (IV) readily precipitate out from the mixture, leaving behind undesirable hazardous by-products (and any unreacted starting materials which may be re-used in subsequent reactions) and can then be converted to the high purity tetrazoles (I). The conversion of the salts (IV) to the tetrazoles (I) can be accomplished, for example, by treatment with an acid, such as dilute HCl as described hereinafter in the Examples.

The preparation of tetrazoles of structure (I) via the salts (IV) is a very efficient process and provides a broad general process for the preparation of salts of tetrazoles of structure (I) by providing a convenient, safe and efficient preparation of the 'free' tetrazoles of structure (I).

The present invention therefore provides in a further aspect a process for preparing a compound of structure (V):

in which $R^1$ is $C_{1-6}$alkyl, optionally substituted phenyl or optionally substituted phenyl$C_{1-6}$alkyl, and X is an ion, characterised in that the compound is in solid form which comprises reacting a compound of structure (I) with a compound providing the source of the ion X.

Suitable and preferred groups $R^1$ are as described for structure (I). Suitable ions X include, for example, alkali metal ions such as lithium, sodium or potassium; group II ions such as calcium and magnesium; and ammonium ions of structure $N^+(R)_3$ in which each group R is hydrogen or $C_{1-6}$alkyl, provided that all three R groups cannot be hydrogen. Other groups X will be apparent to those skilled in the art.

Suitable compounds providing the source of ion X will be apparent to those skilled in the art, and include, for example, alkali metal alkoxides such as sodium methoxide, and soluble ion alkanoate salts such as salts of alkyl-2-hexanoic acids, in particular sodium or potassium ethyl hexanoate as hereinafter described. Alternative ion sources include, for example, alkali metal halides such as sodium iodide, alkali metal acetates such as sodium trifluoroacetate, and ion exchange resins loaded with the ion X as appropriate.

It will be apparent to those skilled in the art that the salts (V) can not only be prepared from the free tetrazoles (I) but can also be prepared by conversion from a different salt (V), for example via anion exchange using a suitable anion exchange resin. Thus, the source of ion X can, in practice, also be a compound of structure (V) itself.

It has been found that the salts of structure (I) can be isolated in solid form and as such are very stable and can be readily transported in pure form.

In a still further aspect there is therefore provided compounds of structure (V):

or a hydrate or solvate thereof, in which $R^1$ is $C_{1-6}$alkyl, optionally substituted phenyl or optionally substituted phenyl$C_{1-6}$alkyl, and X is an ion, characterised in that the compound (V) is in solid form. Suitable values of $R^1$ and X are as described above.

The following examples serve to illustrate the invention. Temperatures are recorded in degrees centigrade.

EXAMPLE 1

Anhydrous sodium salt of ethyl-5-tetrazole carboxylate starting from ethyl cyanoformate.

2,6-Lutidine (115 ml) was stirred under nitrogen and trifluoroacetic acid (20.5 ml) added cautiously over 15 minutes, maintaining the temperature at +5° to +10° C. by cooling in an ice bath. Powdered sodium azide (17.8 g) was added, followed by ethyl cyanoformate (24.8 g) and the reaction mixture heated slowly to ca. 80° C. The mixture was stirred at 75° to 80° C. for 5.5 hours, allowed to cool to room temperature and filtered. The white crystals were washed with ethyl acetate (3×50 ml) and dried in vacuo to constant weight.

Yield of sodium salt: 34.37 g (83.8%)
Purity by hplc analysis: 95.3% as sodium salt
Azide content: none detected, <0.1%.

EXAMPLE 2

Purified ethyl-5-tetrazole carboxylate

The intermediate sodium salt (equivalent to 33 g of pure material), prepared as described in Example 2(a), was suspended in a mixture of saturated brine (100 ml) and ethyl acetate (100 ml), and sodium nitrite (5.2 g) added. The mixture was cooled to ca. 10° C. and cautiously treated with concentrated hydrochloric acid (60 ml) with ice cooling. Further sodium chloride was added to saturate the aqueous phase.

The phases were separated and the aqueous phase further extracted with ethyl acetate (2×50 ml). The combined ethyl acetate phases were evaporated on a rotary evaporator to about 65 g and treated with toluene (65 g). The mixture was again evaporated to about 65 g to give a suspension of the product as a crystalline solid. This was collected by filtration, washed with toluene and dried.

Yield 25.6 g (89.6%)
Purity by hplc analysis 99.5% as free ester

EXAMPLE 3

Potassium salt of ethyl-5-tetrazole carboxylate starting from ethyl cyanoformate a) Intermediate sodium salt 2,6-Lutidine (115 ml) was stirred under nitrogen and cooled in an ice bath. Trifluoroacetic acid (20.5 ml) was added cautiously over 15 minutes, maintaining the temperature at +5° to +12° C., followed by sodium azide (17.8 g) and the mixture stirred well. Ethyl cyanoformate (24.8 g) was then added over about 2 minutes and the reaction mixture heated slowly to ca. 80° C. The mixture was stirred at 75° to 80° C. for 3.5 hours, allowed to cool to room temperature and filtered. The white crystals were washed with ethyl acetate (4×20 ml) and dried in vacuo.

Yield of sodium salt: 34.0 g (82.9%)
Purity by hplc analysis: 95.5% as sodium salt b) Conversion to the potassium salt The sodium salt prepared in a) contained a trace of unreacted sodium azide and small amounts of other impurities. These were removed and the material converted to the potassium salt as follows:

The intermediate sodium salt (14 g) was dissolved in ice-cold water (50 ml) and treated with sodium nitrite (1.5 g). A mixture of conc. hydrochloric acid (15 ml) and water (35 ml) was then added slowly, keeping the temperature below 5° C. The mixture was stirred for 15 minutes, then treated with urea (1.6 g) to destroy the excess nitrous acid. When gas evolution had subsided the solution was saturated with sodium chloride (30 g) and extracted with ethyl acetate (100 ml). The aqueous phase was further extracted with ethyl acetate (2×50 ml) and the combined ethyl acetate extracts washed with saturated brine (50 ml) and dried by stirring with magnesium sulphate (30 g) for 30 minutes.

The mixture was filtered, the drying agent washed with ethyl acetate and the combined filtrate and washings treated slowly with a 2.16M solution of potassium-2-ethyl hexanoate in 2-propanol (50 ml). The mixture was stirred for 10 minutes, the crystals collected by filtration, washed with ethyl acetate (3×25 ml) and dried in vacuo to constant weight.

Yield 12.9 g

Purity by hplc analysis 99.9% as potassium salt.

EXAMPLE 4

Crystalline hydrate of the sodium salt of ethyl-5-tetrazole carboxylate, starting from ethyl cyanoformate a) Intermediate sodium salt 2,6-Lutidine (100 ml) was stirred under nitrogen, and cooled in an ice-bath. Trifluoroacetic acid (5.0 ml) was added cautiously over 15 minutes, maintaining the temperature at +5° to +12° C., followed by sodium azide (17.8 g) and the mixture stirred well for 15 minutes. Ethyl cyanoformate (24.8 g) was then added over about 3 minutes and the reaction mixture heated slowly to ca. 80° C. After an initial exotherm in which the temperature reached 94° C., the mixture was stirred at 80° C. for 4.0 hours, cooled to room 10° C. and filtered. The white crystals were washed with a little 2,6-lutidine, then slurried with ethyl acetate (130 ml). The product was filtered, washed with ethyl acetate (50 ml) and dried in vacuo.

Yield of sodium salt: 39.4 g (96.0%)

Purity by hplc analysis: 90.0% as sodium salt b) Sodium salt hydrate

The sodium salt (30 g) and sodium nitrite (1.75 g) were dissolved in water (75 ml), covered with ethyl acetate (100 ml) and cooled 10° C. 2M hydrochloric acid (120 ml) was then added slowly with stirring, and the mixture stirred for 30 minutes, allowing the temperature to rise to 20° C. The phases were separated, the aqueous phase saturated with sodium chloride and further extracted with ethyl acetate (3×50 ml). The combined ethyl acetate phases were treated slowly with a solution of sodium-2-ethyl hexanoate (31.0 g) in ethyl acetate (100 ml) to precipitate the product as fine needles. These were collected, washed with ethyl acetate, and dried in air.

The product was shown to be crystalline by X-ray powder diffraction. Peaks were recorded from 2.5 to 34.5 degrees 2 theta. The following significant d values were observed (Å units):

14.418,8.277,7.210,7.030,5.460,4.983,4.811,4.613,4.391, 4.086,3.880,3.686,3.532,3.289, 3.163,3.090,2.922,2.741 and 2.672

The infra-red spectrum was significantly different from that of the product of Example 1, and showed strong bands assigned to bound water at 3565 and 3935cm$^{-1}$.

Yield: 31.8 g

Purity by hplc analysis: 81.9% as sodium salt [theory for dihydrate 82%].

EXAMPLE 5

Anhydrous sodium salt of ethyl-5-tetrazole carboxylate from the hydrate

The hydrate from Example 4 was dried in vacuo, with a loss in weight of 17.7%. The product gave an infra-red spectrum indistinguishable from that of the product of Example 7.

EXAMPLE 6

Anhydrous sodium salt of ethyl-5-tetrazole carboxylate from the isolated ester and sodium ethoxide Sodium ethoxide in ethanol (3.56 g of a 21% wt/wt solution) was added dropwise to a solution of ethyl-5-tetrazole carboxylate (1.55 g) in diethyl ether (10 ml) and the mixture stirred for 18 hours at room temperature. The mixture was chilled, stirred for 20 minutes, and filtered. The product was washed on the filter with cold ether and dried.

Yield 1.64 g

Purity by hplc analysis: 93% as sodium salt.

EXAMPLE 7

Anhydrous sodium salt of ethyl-5-tetrazole carboxylate from the isolated ester and sodium-2-ethyl hexanoate Ethyl-5-tetrazole carboxylate (5.0 g) was dissolved in ethyl acetate (40ml) and treated with a solution of sodium-2-ethyl hexanoate (6.5 g) in ethyl acetate (15 ml) over about 30 minutes with stirring at room temperature. The white suspension was diluted with ethyl acetate (50 ml) and filtered. The product was washed on the filter with ethyl acetate and dried in vacuo over phosphorous pentoxide.

Yield 5.60 g (97%)

The product was shown to be crystalline by X-ray powder diffraction. Peaks were recorded from 2.5 to 34.5 degrees 2 theta. The following significant d values were observed (Å units):

7,039,6.135,5.467,4.989,4.613,4.087,3.688,3.533,3.395, 3.165,3.080,2.968,2.742 and 2.673

Infra-red spectrum (nujol mull): Characteristic strong bands were observed at 1735, 1728 and 1718 cm$^{-1}$, (ester carbonyl) and at 1239,1220,1174,1158,1059, 1041 and 1028 cm$^{-1}$.

| | Elemental analysis: | | | |
|---|---|---|---|---|
| Requires | C 29.28% | H 3.07% | N 34.14% | Na 14.01% |
| Found | C 29.08% | H 2.98% | N33.84% | Na 14.10% |

Purity by hplc analysis: 100% as sodium salt.

EXAMPLE 8

Potassium salt of ethyl-5-tetrazole carboxylate from the isolated ester and potassium- 2-ethyl hexanoate Ethyl-5-tetrazole carboxylate (5.0 g) was dissolved in ethyl acetate (150 ml) and treated with a 2.16M solution of potassium-2-ethyl hexanoate in 2-propanol (20 ml) over about 2 minutes with stirring at room temperature. The addition was interrupted briefly to allow the product to crystallise. The product was viewed under a polarising microscope and found to consist of rectangular prisms. These were collected by filtration, washed on the filter with ethyl acetate (25 ml, 50 ml) and dried in air.

Yield 6.0 g (94.6%)

Purity by hplc analysis: 99.70% as potassium salt

The product was shown to be crystalline by X-ray powder diffraction. Peaks were recorded from 2.5 to 34.5 degrees 2 theta. The following significant d values were observed (Å units):

10.793,7.632,7.431,7.107,6.503,5.917,5.236,4.808,4.291, 3.994,3.821,3.757,3.714,3.610, 3.553,3.435,3.298,3.229,3.166,3.098,3.046,3.010,2.870,2.774 and 2.646

Infra-red spectrum (nujol mull):

Characteristic strong bands were observed at 1718 and 1706 cm$^{-1}$, (ester carbonyl) and at 1232, 1169,1157,1058, 1042 and 1020 cm$^{-1}$.

We claim:

1. A process for preparing a compound of structure (I):

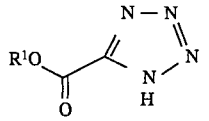  (I)

or a hydrate or solvate thereof in which $R^1$ is $C_{1-6}$alkyl, optionally substituted phenyl or optionally substituted phenyl$C_{1-6}$alkyl, which comprises reacting an azide of structure (II) with a cyanoformate of structure (III)

  (II)

  (III)

in which M is an alkali metal atom, and $R^1$ is as described for structure (I), to form an intermediate salt of structure (IV):

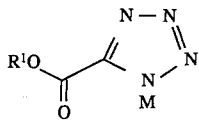  (IV)

in which $R^1$ is as described for structure (I) and M is as described for structure (II) followed by conversion of the salt (IV) to the free tetrazole (I) or to a hydrate or solvate thereof.

2. A process according to claim 1 in which $R^1$ is $C_{1-4}$alkyl.

3. A process according to claim 2 in which M is selected from sodium or potassium.

4. A compound of structure (V):

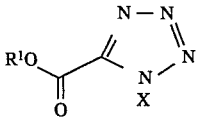  (V)

or a solvate or hydrate thereof in which $R^1$ is $C_{1-6}$alkyl, optionally substituted phenyl or optionally substituted phenyl$C_{1-6}$alkyl, and X is an ion, in solid form, provided that X is not an ion of formula $N^+(R)_3$ in which each group R is hydrogen.

5. A compound according to claim 4 in which X is an alkali metal atom.

6. A compound according to claim 5 in which X is sodium or potassium.

7. A process for preparing a compound of structure (V) which comprises reacting a compound of structure (I) with a compound providing a suitable source of the ion X.

8. A process according to claim 7 in which the compound providing the source of the ion X is 2-ethyl hexanoic acid.

* * * * *